(12) United States Patent
Miyashita et al.

(10) Patent No.: US 9,590,183 B2
(45) Date of Patent: Mar. 7, 2017

(54) ORGANIC COMPOUND AND ORGANIC LIGHT-EMITTING DEVICE INCLUDING THE SAME

(71) Applicant: CANON KABUSHIKI KAISHA, Tokyo (JP)

(72) Inventors: Hirokazu Miyashita, Tokyo (JP); Jun Kamatani, Tokyo (JP); Akihito Saitoh, Gotemba (JP); Yosuke Nishide, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 359 days.

(21) Appl. No.: 14/360,287

(22) PCT Filed: Oct. 22, 2012

(86) PCT No.: PCT/JP2012/077818
§ 371 (c)(1),
(2) Date: May 22, 2014

(87) PCT Pub. No.: WO2013/077142
PCT Pub. Date: May 30, 2013

(65) Prior Publication Data
US 2014/0264318 A1    Sep. 18, 2014

(30) Foreign Application Priority Data

Nov. 24, 2011    (JP) ................. 2011-256747

(51) Int. Cl.
*H01L 51/00*    (2006.01)
*H01L 51/50*    (2006.01)
(Continued)

(52) U.S. Cl.
CPC .......... *H01L 51/0058* (2013.01); *C07C 15/20* (2013.01); *C07C 25/22* (2013.01);
(Continued)

(58) Field of Classification Search
CPC . C07C 15/20; C07C 2101/14; C07C 2103/54; C07C 211/61; C07C 255/52;
(Continued)

(56) References Cited

U.S. PATENT DOCUMENTS 7,183,010 B2 *   2/2007   Jarikov ................. C09K 11/06
                                                    313/504

FOREIGN PATENT DOCUMENTS

WO        02/100977 A1    12/2002

OTHER PUBLICATIONS

E. Rachin. "Theoretic Cancerogenicity of Seven-Ring Benzene Hydrocarbons", Bulgarian Academy of Sciences, Communications of the Department of Chemistry, 1988, pp. 69-77, vol. 21, No. 1.
(Continued)

*Primary Examiner* — Dawn Garrett
(74) *Attorney, Agent, or Firm* — Canon U.S.A., Inc. IP Division

(57) ABSTRACT

The present invention provides a novel stable benzo[a]naphtho[2,1-c]tetracene compound and an organic light-emitting device including the compound. Provided is an organic compound represented by Formula [1].
(Continued)

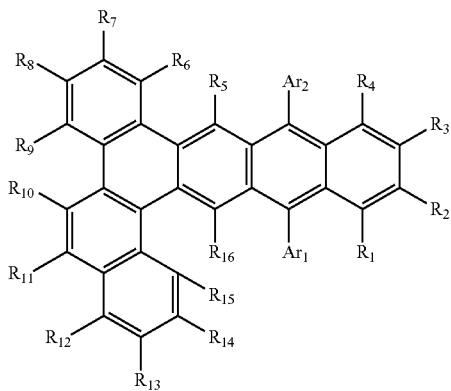

In Formula [1], $R_1$ to $R_{16}$ are each independently selected from the group consisting of a hydrogen atom, a halogen atom, an alkyl group having 1 to 4 carbon atoms, a cyano group, a diphenylamino group, a pyridyl group, and an aryl group.

10 Claims, 2 Drawing Sheets

(51) Int. Cl.
    C07C 15/20      (2006.01)
    C09K 11/06      (2006.01)
    H05B 33/14      (2006.01)
    C07C 255/52     (2006.01)
    C07C 211/61     (2006.01)
    C07D 213/06     (2006.01)
    C07D 213/16     (2006.01)
    C07C 25/22      (2006.01)
    C07D 213/53     (2006.01)
    C09B 3/78       (2006.01)

(52) U.S. Cl.
    CPC ......... C07C 211/61 (2013.01); C07C 255/52 (2013.01); C07D 213/06 (2013.01); C07D 213/16 (2013.01); C07D 213/53 (2013.01); C09B 3/78 (2013.01); C09K 11/06 (2013.01); H01L 51/50 (2013.01); H05B 33/14 (2013.01); *C07C 2101/14* (2013.01); *C07C 2103/54* (2013.01); *C09K 2211/1011* (2013.01); *H01L 51/0056* (2013.01); *H01L 51/504* (2013.01); *Y02B 20/181* (2013.01)

(58) Field of Classification Search
    CPC .... C07C 25/22; C07D 213/06; C07D 213/16; C07D 213/53; C09B 3/78; C09K 11/06; C09K 2211/1011; H01L 51/0056; H01L 51/0058; H01L 51/50; H01L 51/504; H05B 33/14; Y02B 20/181
    See application file for complete search history.

(56) References Cited

OTHER PUBLICATIONS

Cohen, D. et al., "Reactions of 5,6-Chrysenequinodimethane", Journal of the Chemical Society Section C Organic, 1967, pp. 1499-1503, 16.
Millar, Ian T. et al Diels-Alder reactions of 9,10-Anthraquinodimethane, 1965, No. 15, 369-70.
Blatter, Karsten et al, Diels-Alder reactions, Feb. 7, 1989, 1351-6.

* cited by examiner

ORGANIC COMPOUND AND ORGANIC LIGHT-EMITTING DEVICE INCLUDING THE SAME

TECHNICAL FIELD

The present invention relates to a novel organic compound and an organic light-emitting device including the organic compound.

BACKGROUND ART

An organic light-emitting device includes an anode, a cathode, and an organic compound layer disposed therebetween. Electrons and holes are injected from the electrodes into the organic compound layer to generate excitons of a light-emitting organic compound in the organic compound layer, and light is emitted when the excitons return to the ground state.

The organic light-emitting device is also referred to as organic electroluminescent device or organic EL device. Organic light-emitting devices have remarkably progressed recently, and low driving voltages, high luminance, various emission wavelengths, rapid response, and reductions in size and weight of light-emitting devices are possible.

In the organic light-emitting devices, however, the organic compound itself emits light, and thereby the lifetime is short, and there is a demand for further extension of the lifetime.

NPL 1 describes theoretical calculation of compounds represented by the following Structural Formula A. NPL 2 describes a method of synthesizing compounds represented by the following Structural Formula A.

NPL 1 and NPL 2, however, do not describe light emission characteristics of compounds represented by Structural Formula A at all.

[Chem. 1]

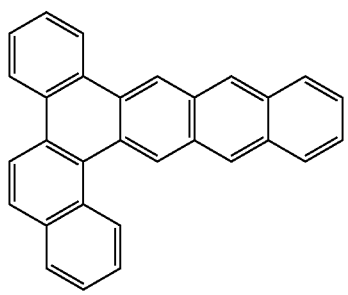 [SMILES: c1ccc2cc3cc4c(cc3cc2c1)c1ccccc1c1ccc2ccccc2c14]

Structural Formula A

The compounds described in NPLs 1 and 2 have highly reactive sites and thereby show low stability against oxidation. Furthermore, the intermolecular interaction is strong due to the high flatness of the molecules. The compounds therefore have low amorphous properties to be easily crystallized.

Such compounds having low stability against oxidation and low amorphous properties are not preferred as materials to be used for organic light-emitting devices.

CITATION LIST

Non Patent Literature

NPL 1 Izvestiya po khimiya, 21(1), 69-77 (1988)
NPL 2 Journal of the Chemical Society C, 16, 1499-1503 (1967)

SUMMARY OF INVENTION

The present invention provides an organic compound having high stability against oxidation and a high amorphous property.

Accordingly, the present invention provides an organic compound represented by the following Formula [1]:

[Chem. 2]

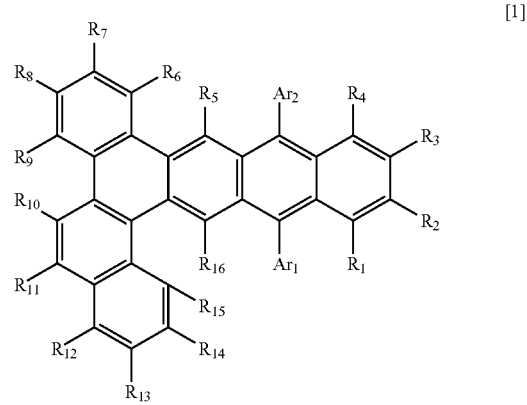

[1]

In Formula [1], $R_1$ to $R_{16}$ each independently selected from a hydrogen atom, a halogen atom, an alkyl group having 1 to 4 carbon atoms, a cyano group, a diphenylamino group, a pyridyl group, and an aryl group.

The diphenylamino, the pyridyl group, and the aryl group each optionally have at least one substituent selected from a methyl group, an ethyl group, an iso-propyl group, a t-butyl group, and a fluorine atom.

$Ar_1$ and $Ar_2$ are each any of a phenyl group, a biphenyl group, a terphenyl group, and a naphthyl group.

$Ar_1$ and $Ar_2$ each optionally have at least one substituent selected from a methyl group, an ethyl group, an iso-propyl group, a t-butyl group, and a fluorine atom.

DESCRIPTION OF EMBODIMENT

Figure 1:
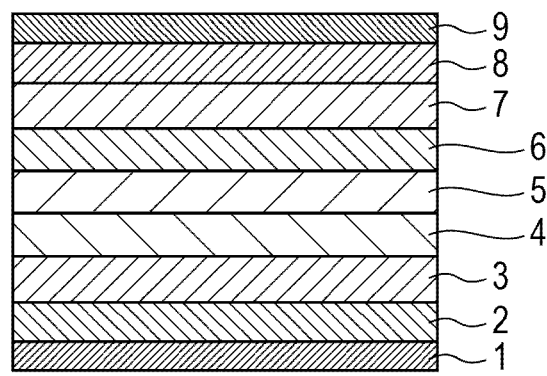
FIG. 1 is a schematic cross-sectional view illustrating an example of the organic light-emitting device of a light-emitting layer lamination type according to an embodiment.

The present invention relates to an organic compound represented by the following Formula [1]:

[Chem. 3]

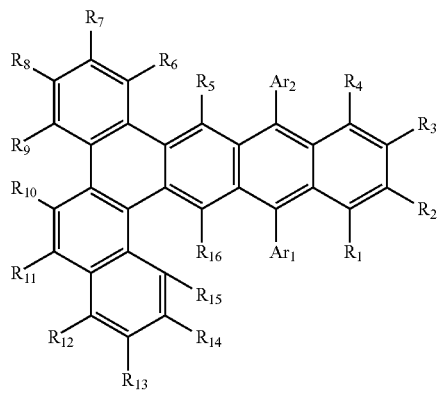

[1]

In Formula [1], $R_1$ to $R_{16}$ each independently selected from a hydrogen atom, a halogen atom, an alkyl group having 1 to 4 carbon atoms, a cyano group, a diphenylamino group, a pyridyl group, and an aryl group.

The diphenylamino, the pyridyl group, and the aryl group each optionally have at least one substituent selected from a methyl group, an ethyl group, an iso-propyl group, a t-butyl group, and a fluorine atom.

$Ar_1$ and $Ar_2$ are each any of a phenyl group, a biphenyl group, a terphenyl group, and a naphthyl group.

$Ar_1$ and $Ar_2$ each optionally have at least one substituent selected from a methyl group, an ethyl group, an iso-propyl group, a t-butyl group, and a fluorine atom.

The organic compound according to the present invention has a basic skeleton having the same structure as that of unsubstituted benzo[a]naphtho[2,1-c]tetracene.

The organic compound according to the present invention has aryl groups at the positions of $Ar_1$ and $Ar_2$ and is therefore stable against oxidation. In addition, the basic skeleton itself has distortion and therefore has low flatness. Furthermore, the aryl groups at the positions of $Ar_1$ and $Ar_2$ effectively reduce intermolecular interaction. Comparison of the organic compound according to the present invention with other organic compounds Example Compound A1 according to the embodiment will be compared with an organic compound represented by Formula (2).

The organic compound represented by Formula (2) is a compound described in NPLs 1 and 2.

[Chem. 4]

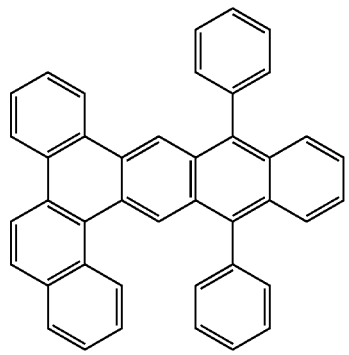 [SMILES: c1ccc(-c2c3ccccc3c(-c3ccccc3)c3cc4c(cc23)c2ccccc2c2ccc3ccccc3c24)cc1]

A1

[Chem. 5]

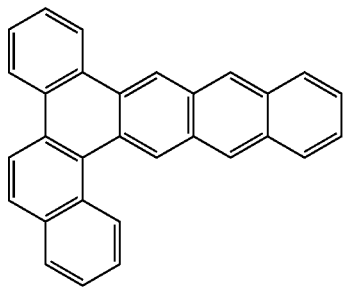

(2)

The organic compound used in an organic light-emitting device is required to be stable against an oxidation-reduction reaction.

This is because that the organic light-emitting device emits light by an exciton of the organic compound, the exciton being generated by recombination of a hole generated by an oxidation reaction at the anode interface and an electron generated by a reduction reaction at the cathode interface.

The organic compound according to the present invention has a substituent at a specific position to reduce the reactivity of a highly reactive site in the basic skeleton and is therefore stable against oxidation.

The reason that the organic compound according to the present invention is more stable against oxidation than the compound (2) will be described with reference to the structures of the compounds.

Among fused ring compounds, compounds having a structure in which a plurality of benzene rings is linearly fused are called acene. A characteristic of the acene compound is that the structural stability decreases with an increase in the number of the fused benzene rings.

For example, in anthracene, which is a typical acene compound, the benzene rings at both ends function as electron donors to increase the electron density of the central benzene ring.

As a result, the central benzene ring of anthracene tends to be oxidized. That is, the active sites unstable against oxidation in anthracene are the 9- and 10-positions at the center.

[Chem. 6.]

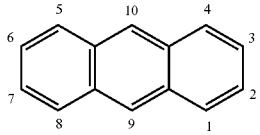

The active sites unstable against oxidation can be stabilized by introducing substituents thereto.

Introduction of substituents to the 9- and 10-positions changes the electron density state in the molecule. In addition, the introduction of substituents causes steric hindrance to inhibit other molecules from approaching the active sites.

That is, though a fused ring compound having a structure in which a plurality benzene rings is linearly fused, such as acene, is unstable due to the active sites, the stability against oxidation can be enhanced by introducing substituents to the active sites.

Compound (2) partially has a structure having linearly fused unsubstituted benzene rings and is unstable against oxidation.

Example Compound A1 according to the embodiment and Compound (2) were subjected to cyclic voltammetry (CV) measurement. Sweeping was performed by repeating oxidation-reduction 20 times, and both compounds were compared for stability against oxidation-reduction on the basis of the changes in cyclic voltammogram.

Figure 3:
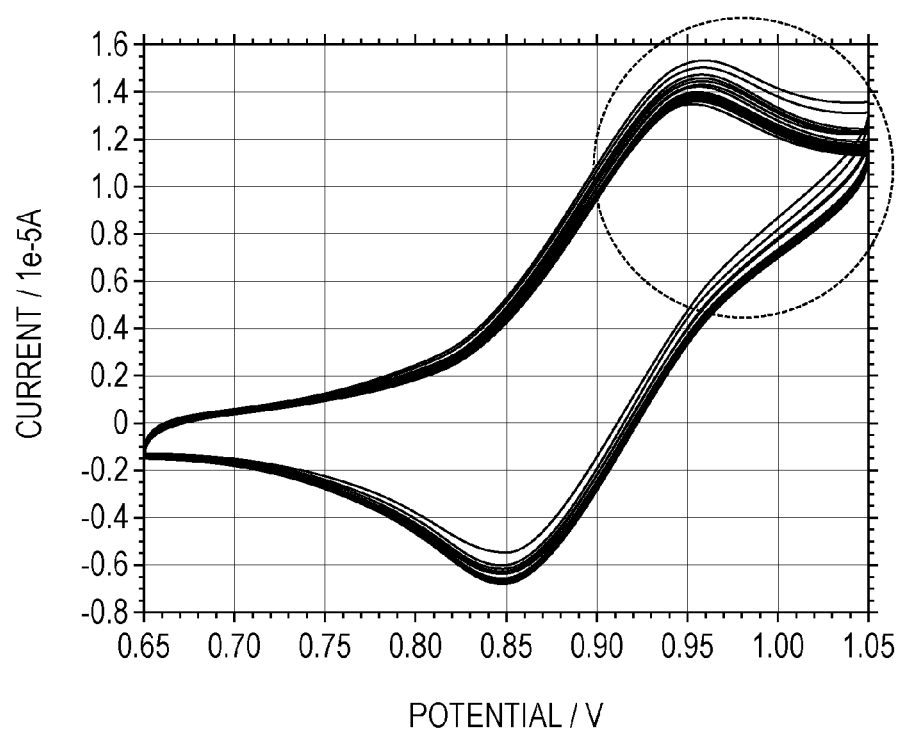
FIG. 3 is a cyclic voltammogram of compound (2) according to the embodiment.

FIG. 3 shows the CV measurement results of Compound (2).

The CV measurement was performed in a 0.1 M solution of tetrabutylammonium perchlorate in acetonitrile using Ag/Ag$^+$ as the reference electrode, Pt as the counter electrode, and glassy carbon as the working electrode.

The measurement was performed at a voltage sweeping rate of 1.0 V/s with an electrochemical analyzer, model 660C, manufactured by ALS.

In Compound (2), the peak current value changes with an increase of the number of the cycles. In Example Compound A1, however, any change is not recognized in the peak current value.

In particular, the cyclic voltammogram of Compound (2) largely changes in the range indicated by a dotted line.

This means that Compound (2) is changed to another compound in consequence of repetition of the oxidation-reduction reaction. In other words, Compound (2) has low stability against oxidation-reduction.

As described above, in Example Compound A1, which is an organic compound according to the present invention, the compound itself is stable against oxidation compared with Compound (2) and is therefore an organic compound suitable for an organic light-emitting device.

The organic compound used for the organic light-emitting device is required to be capable of forming a thin film having a high amorphous property to show excellent film properties. A high amorphous property is also referred to as low crystallizability.

A molecule having a higher amorphous property has a molecular structure having lower flatness. Accordingly, the amorphous property of a molecule can be determined based on the flatness of a molecular structure.

The crystallizability of a molecule can be determined based on the glass transition temperature of the molecule.

The organic compound according to the present invention has aryl groups at the positions of Ar$_1$ and Ar$_2$ to reduce intermolecular interaction. As a result, the organic compound according to the present invention can form a thin film having a higher amorphous property compared with Compound (2).

Example Compound A1 according to the embodiment and Compound (2) were compared for flatness of the molecular skeletons by molecular orbital calculation using density functional theory at the B3LYP/6-31G* level.

A part of the basic skeleton of the organic compound according to present invention is called a benzo[c]phenanthrene skeleton moiety or an anthracene skeleton moiety as shown in the drawing below.

The benzo[c]phenanthrene site causes distortion in the basic skeleton, and therefore the flatness of the molecular skeleton is lower than those of ordinary fused ring compounds. This reduces intermolecular interaction. In contrast, the flatness of the anthracene site is high.

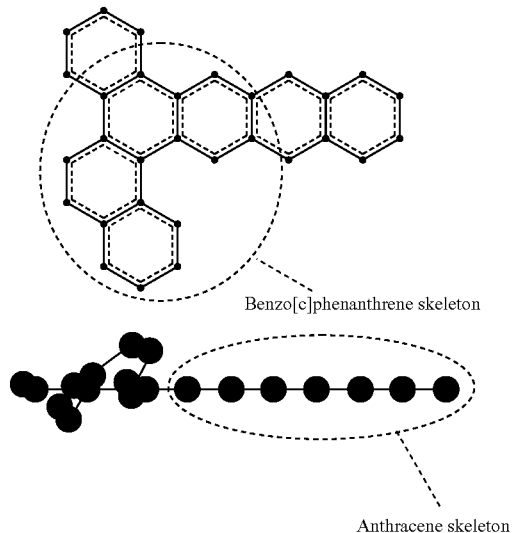

[Chem. 7]

Benzo[c]phenanthrene skeleton

Anthracene skeleton

As shown in Formula (1), the organic compound according to the present invention has Ar$_1$ and Ar$_2$ at the anthracene site to reduce intermolecular interaction. Though the effect can be obtained by introducing a substituent into only one of Ar$_1$ and Ar$_2$, introduction of substituents into the both is preferred.

The positions of Ar$_1$ and Ar$_2$ will be described.

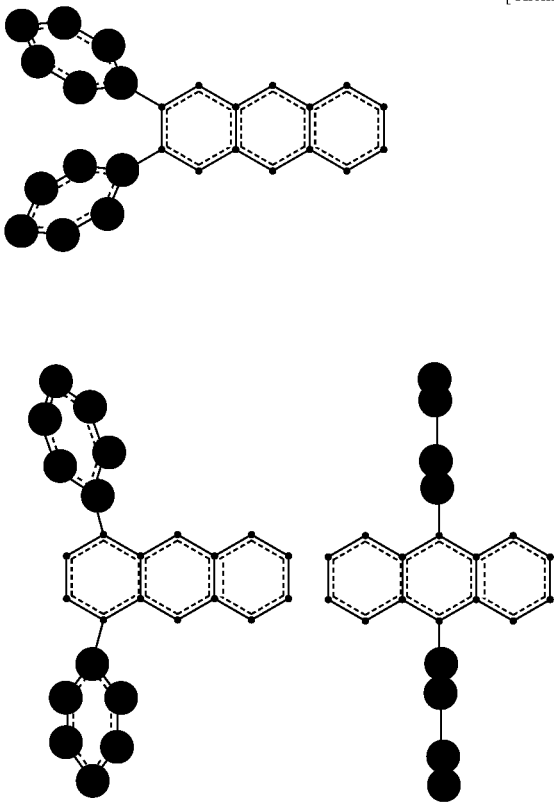

[Chem. 8]

-continued

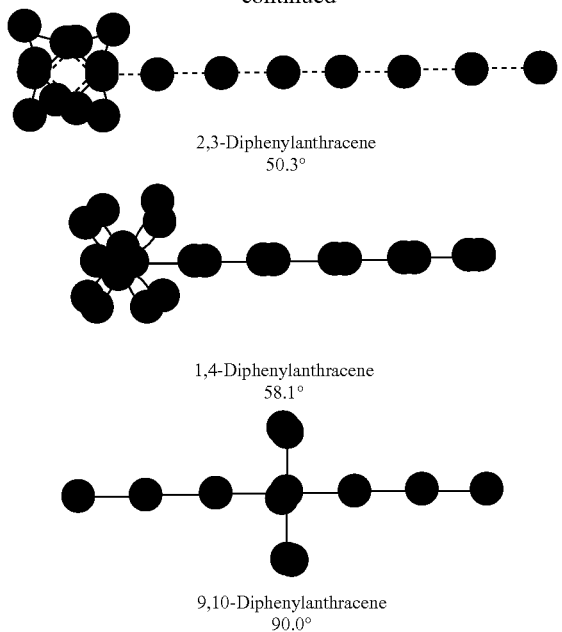

2,3-Diphenylanthracene
50.3°

1,4-Diphenylanthracene
58.1°

9,10-Diphenylanthracene
90.0°

For example, in diphenylanthracene, the dihedral angle of a phenyl group with respect to the molecular plane varies depending on the substitutional positions of the two phenyl groups.

The dihedral angle of the phenyl group is the maximum when the two phenyl groups are present at the 9- and 10-positions. When the dihedral angle is the maximum, the excluded volume effect becomes highest to most effectively reduce intermolecular interaction.

As shown in Table 1, Example Compound A1 has bulky substituents at positions to effectively reduce intermolecular interaction and therefore has a high amorphous property.

In contrast, Compound (2) is unsubstituted and therefore has a low amorphous property. Therefore, Example Compound A1 can form a film having a higher amorphous property compared with Compound (2).

Thus, the organic compound according to the present invention can be used in organic light-emitting devices.

TABLE 1

| Compound | Structural Formula | Molecular plane: perpendicular direction | Molecular plane: parallel direction |
|---|---|---|---|
| Compound (2) | | | |
| Example Compound A1 | | | |

The organic compound according to the present invention is highly stable against oxidation and has a high amorphous property. Accordingly, the organic compound can be used as a material for organic light-emitting devices, in particular, as a host material of a light-emitting layer.

Throughout the specification, a host material is a compound having a largest weight ratio among the compounds constituting a light-emitting layer, and a guest material is a compound having a smaller weight ratio than that of the host material and bearing main light emission among the compounds constituting the light-emitting layer. The guest material is also referred to as a dopant.

The light-emitting layer may further include an assist material. The assist material is a compound having a smaller weight ratio than that of the host material and assisting the light emission of the guest material among the compounds constituting a light-emitting layer. The assist material is also referred to as a second host material.

An organic light-emitting device including the organic compound according to the present invention as a host material of the light-emitting layer shows a high luminous efficiency and a long device lifetime and is therefore an excellent organic light-emitting device.

Examples of the organic compound according to the present invention are shown below, but the organic compounds according to the present invention are not limited to these compounds.

[Chem. 9]

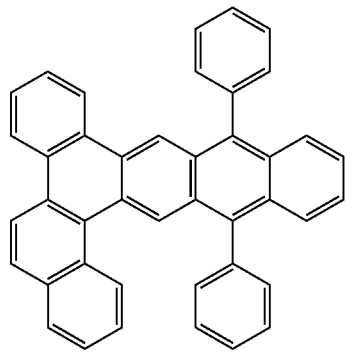 [SMILES: c1ccc(-c2c3ccccc3c(-c3ccccc3)c3cc4c(cc23)c2ccccc2c2ccc3ccccc3c24)cc1]

A1

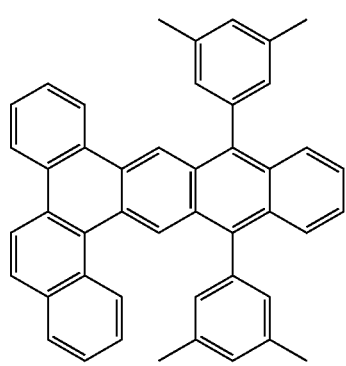

A2

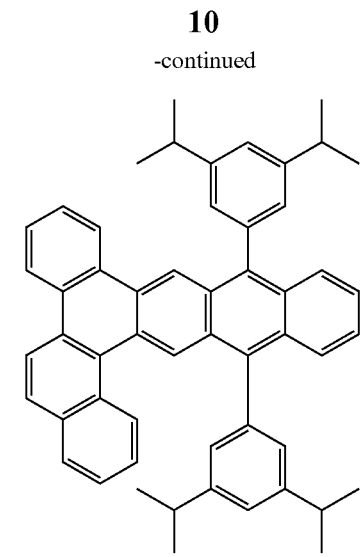

A3

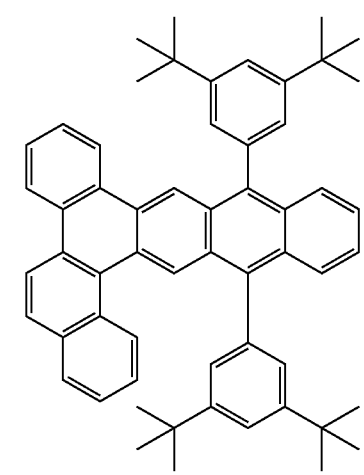

A4

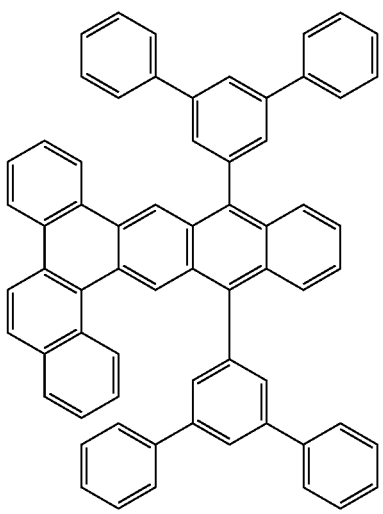

A5

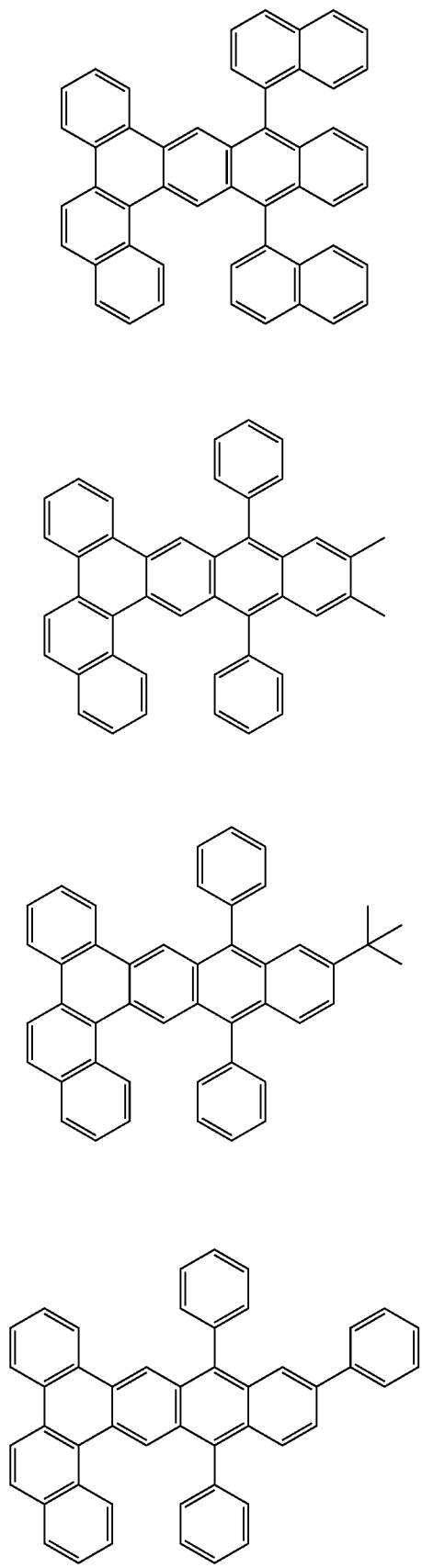
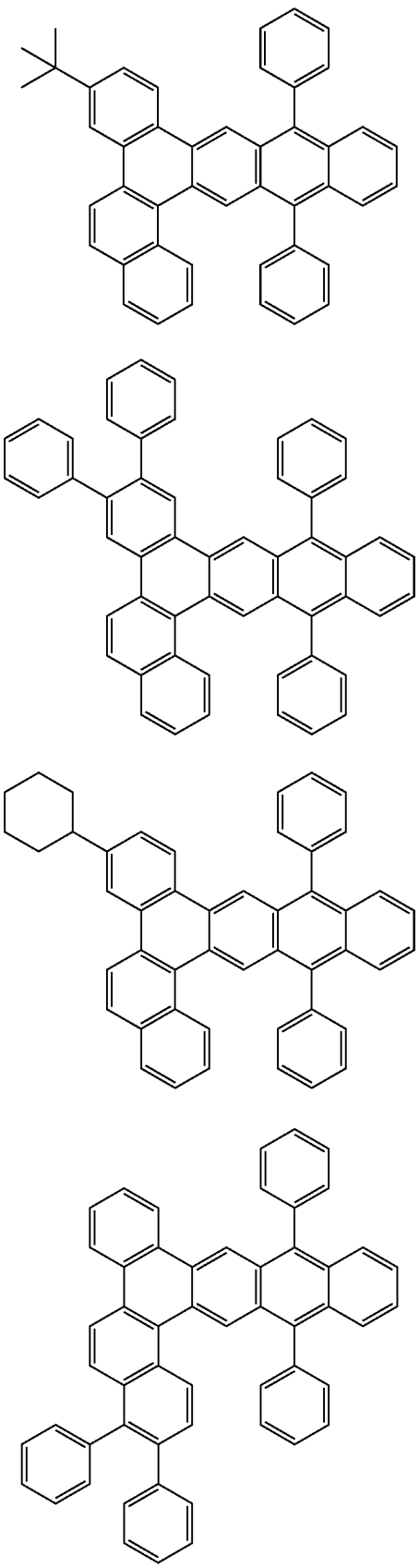

A14
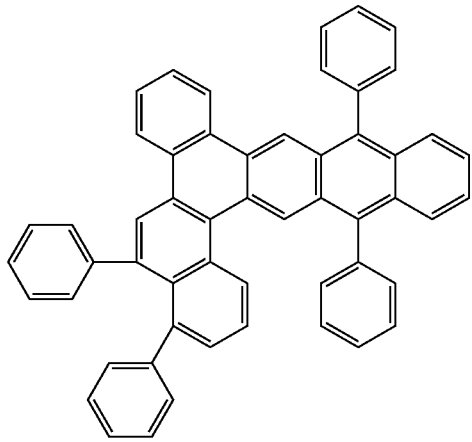
A15
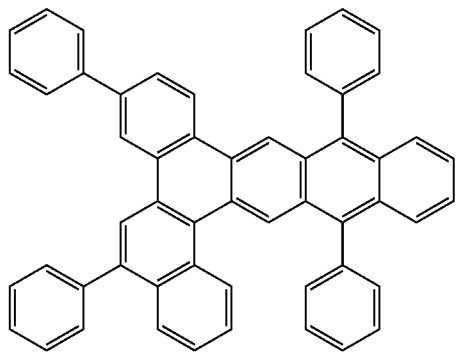
[Chem. 10]
A16
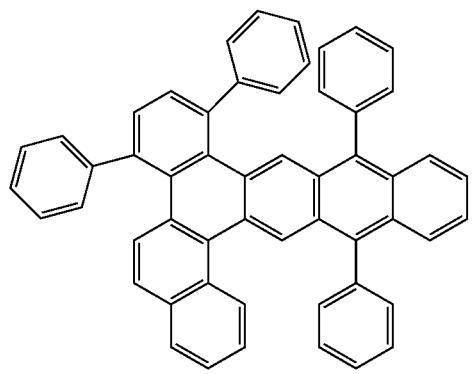
A17
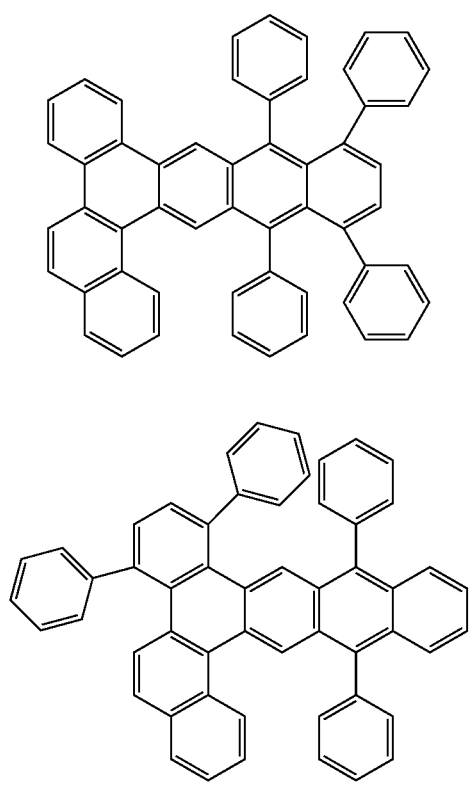
A18
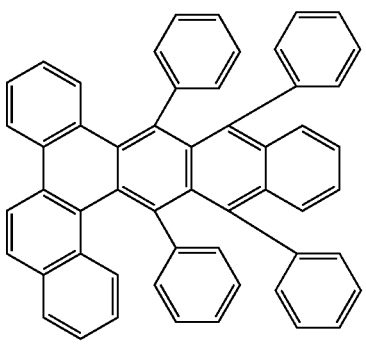
A19
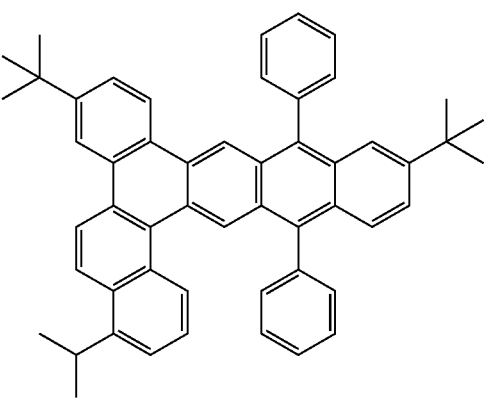
A21
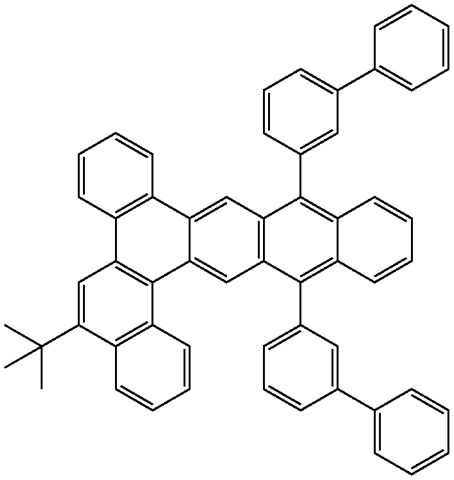

A22
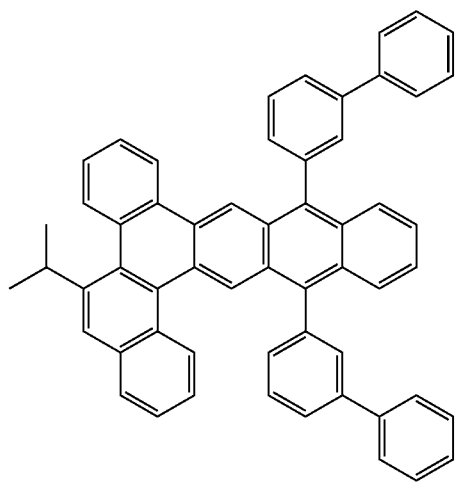
[Chem. 11]
B1
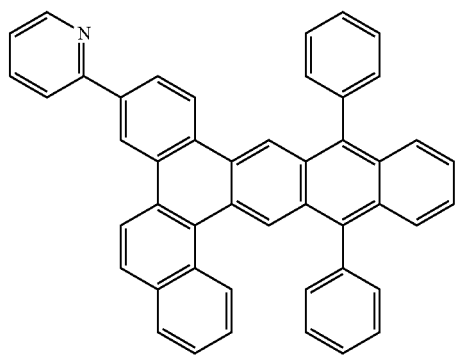
B2
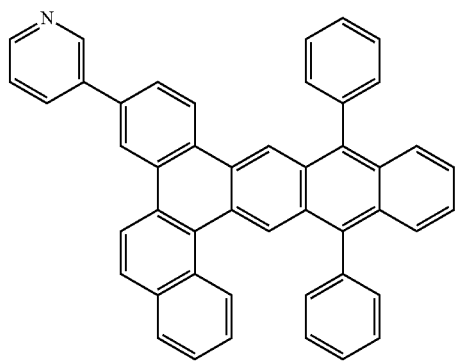
B3
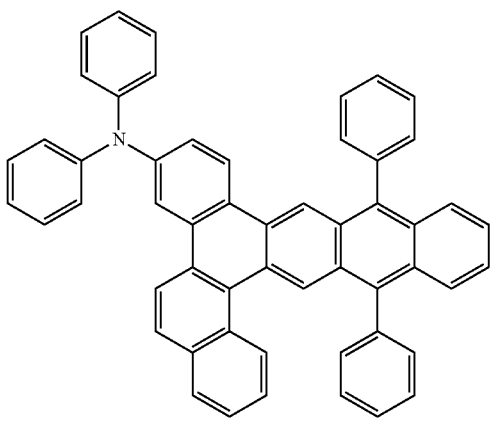
B4
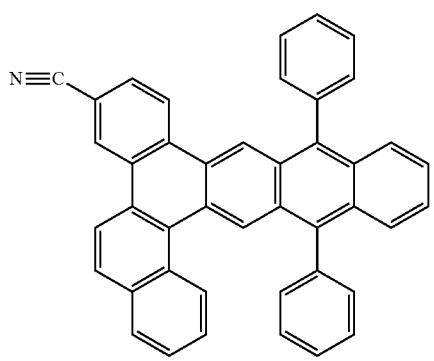
B5
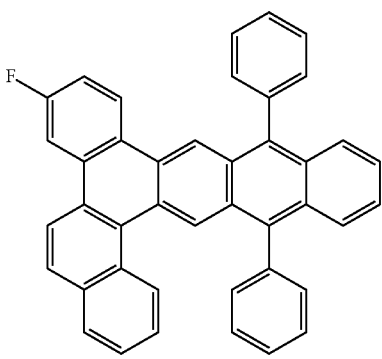

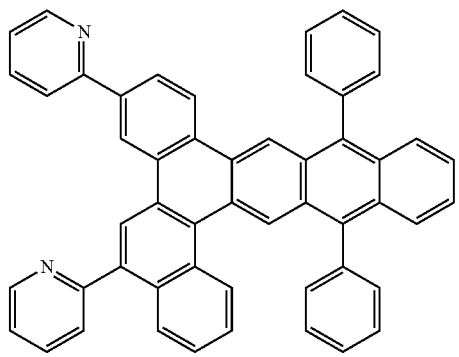 [SMILES: c1ccc(-c2ccc3c(c2)c2cc(-c4ccccc4)c4ccccc4c2c2cc4c(-c5ccccc5)c5ccccc5c(-c5ccccc5)c4cc32)cc1]

B6

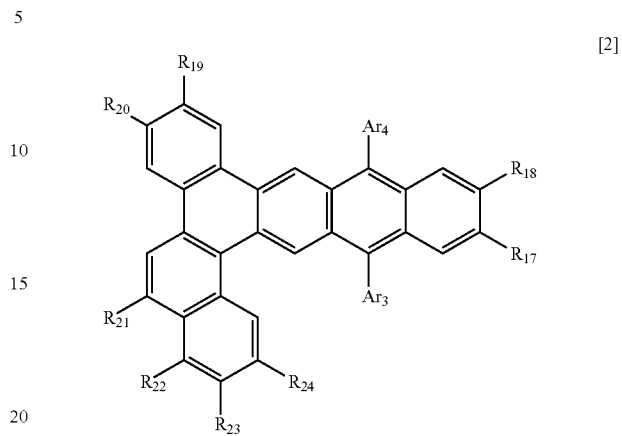

[Chem. 12]

[2]

The compounds belonging to group A are each composed of only hydrocarbons over the entire molecule. Compounds composed of only hydrocarbons have low HOMO energy levels. This means that the compounds have low oxidation potentials and are stable against oxidation.

A low HOMO energy level means that the HOMO energy level is far from the vacuum level and is also expressed as a deep HOMO.

Accordingly, among the organic compounds according to the present invention, the compounds composed of only hydrocarbons belonging to group A are highly stable compounds.

The compounds belonging to group B have hetero atoms in substituents. The hetero atoms change the oxidation potential of molecules, intermolecular interaction, and also electron-transporting ability.

Consequently, the organic compounds can be used as host materials being excellent in adjustment of carrier balance and efficiently generating excitons. The organic compounds can be used, in addition to as the host material, for example, in an electron-transporting layer or electron-injecting layer.

Among the organic compounds according to the present invention, the organic compounds represented by the following Formula [2] are stable because the substituents are hardly brought into contact with each other.

In Formula [2], $R_{17}$ to $R_{24}$ each independently selected from a hydrogen atom, a halogen atom, an alkyl group having 1 to 4 carbon atoms, a cyano group, a diphenylamino group, a pyridyl group, and an aryl group.

The diphenylamino group, the pyridyl group, and the aryl group each optionally have at least one substituent selected from a methyl group, an ethyl group, an iso-propyl group, a t-butyl group, and a fluorine atom.

$Ar_3$ and $Ar_4$ are each any of a phenyl group, a biphenyl group, a terphenyl group, and a naphthyl group.

$Ar_3$ and $Ar_4$ each optionally have at least one substituent selected from a methyl group, an ethyl group, an iso-propyl group, a t-butyl group, and a fluorine atom.

The substituents respectively correspond to those in Formula [1], and the role and effect thereof are the same as those in Formula [1].

Synthesis Route

An example of synthesis route of the organic compound according to the present invention will be described below.

[Chem. 13]

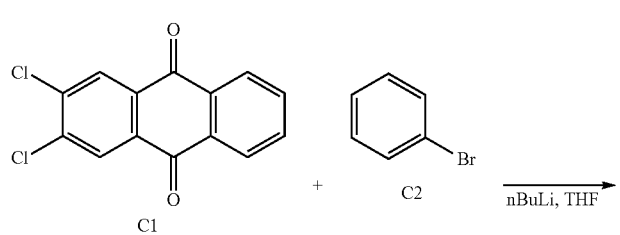
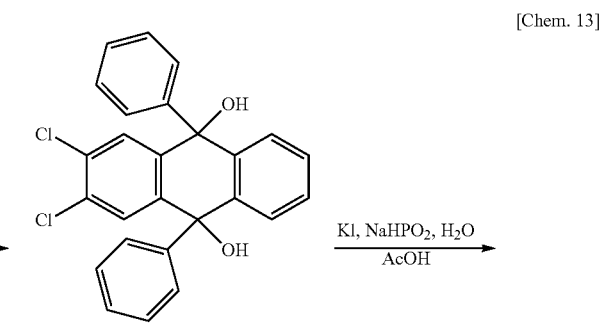

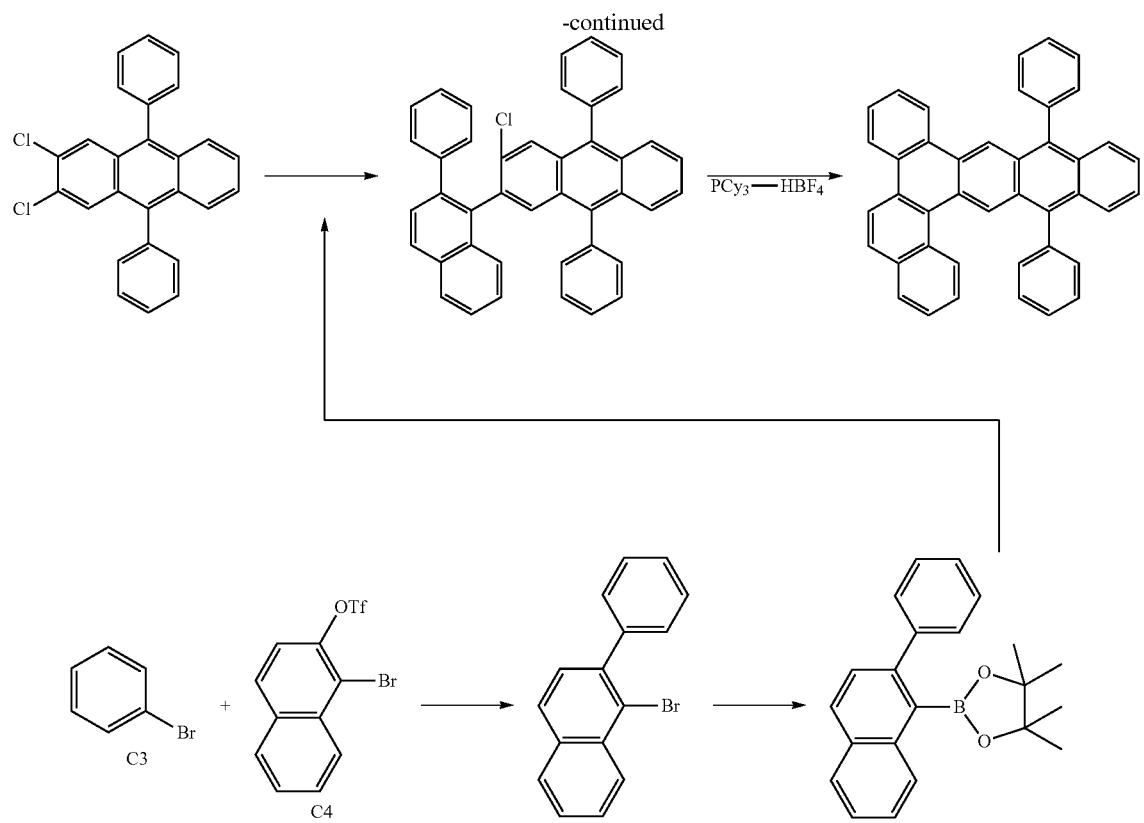
Other Organic Compounds and Raw Materials
Various organic compounds can be synthesized by changing C1 to C4 in the above-mentioned reaction formulae. Specific examples thereof are shown in Table 2 as synthesized compounds. Table 2 also shows the raw materials C1 to C4 for preparing the synthesized compounds.

TABLE 2
| Synthesis Example | C1 | C2 | C3 | C4 | Synthesized compound | Example Compound No. |
|---|---|---|---|---|---|---|
| 1 | 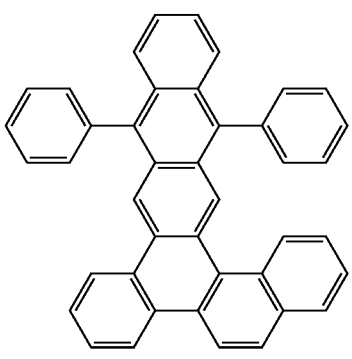 | 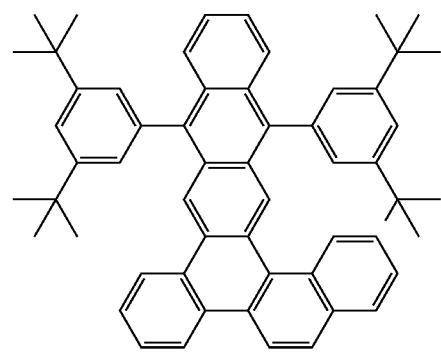 | 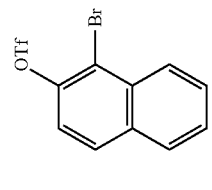 | 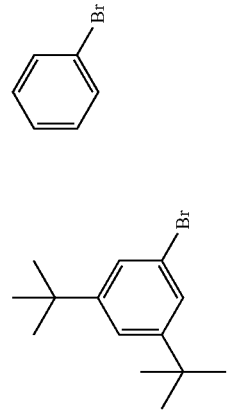 | 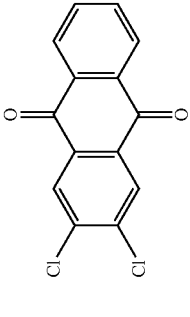 | A1 |
| 2 | 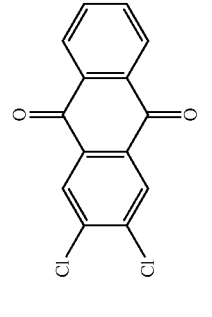 | 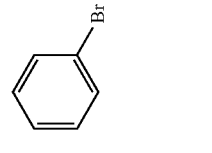 | 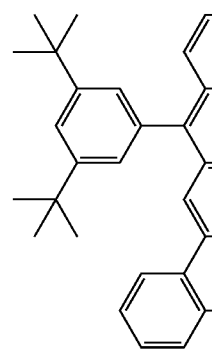 | 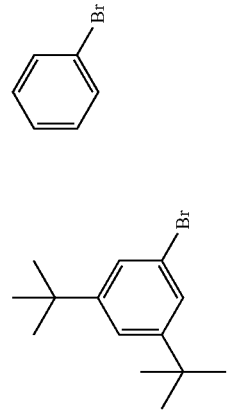 | 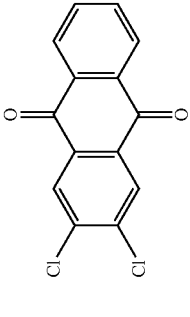 | A4 |

TABLE 2-continued

| Synthesis Example | C1 | C2 | C3 | C4 | Synthesized compound | Example Compound No. |
|---|---|---|---|---|---|---|
| 3 | (naphthalene-fused anthraquinone with 2 Cl) | 1-bromonaphthalene | bromobenzene | 1-bromo-2-triflyloxynaphthalene | (polycyclic aromatic compound) | A6 |
| 4 | (dimethyl-anthraquinone with 2 Cl) | bromobenzene | bromobenzene | 1-bromo-2-triflyloxynaphthalene | (polycyclic aromatic compound) | A7 |

TABLE 2-continued

| Synthesis Example | C1 | C2 | C3 | C4 | Synthesized compound | Example Compound No. |
|---|---|---|---|---|---|---|
| 5 | (phenyl-substituted anthraquinone with 2 Cl) | bromobenzene | bromobenzene | 1-bromo-2-OTf-naphthalene | (polycyclic aromatic structure) | A9 |
| 6 | (dichloroanthraquinone) | bromobenzene | 4-tert-butylbromobenzene | 1-bromo-2-OTf-naphthalene | (polycyclic aromatic structure with tert-butyl) | A10 |

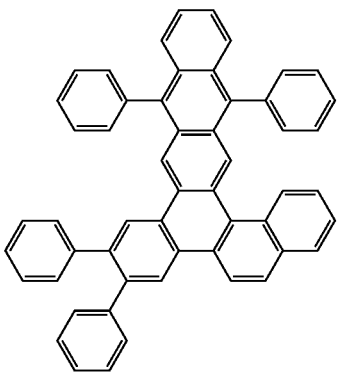

Explanation of Organic Light-Emitting Device According to the Embodiment

An organic light-emitting device according to the embodiment will now be described.

The organic light-emitting device according to the embodiment includes a pair of electrodes, an anode and a cathode, and an organic compound layer disposed therebetween. In this device, the organic compound layer includes the organic compound represented by Formula [1].

The organic compound layer of the organic light-emitting device according to the embodiment may be a monolayer or a multilayer.

Herein, the multilayer includes those appropriately selected from, for example, a hole-injecting layer, a hole-transporting layer, a light-emitting layer, a hole-blocking layer, an electron-transporting layer, an electron-injecting layer, and an exciton-blocking layer. A plurality of layers selected from the above-mentioned layers may be used in combination.

The configuration of the organic light-emitting device according to the embodiment is not limited thereto, and various layer configurations can be employed. For example, an insulating layer may be disposed at the interface between an electrode and an organic compound layer; an adhesive layer or an interference layer may be provided; or an electron-transporting layer or a hole-transporting layer may be composed of two layers having different ionization potentials.

The configuration of the device may be a bottom emission system, which extracts light from the electrode on the substrate side, or a top emission system, which extracts light from the opposite side of the substrate. Alternatively, a configuration in which light is extracted from both sides can also be employed.

The organic light-emitting device according to the embodiment can include the organic compound according to the present invention in the light-emitting layer.

The concentration of the host material in the light-emitting layer of the organic light-emitting device according to the embodiment is 50 wt % or more and 99.9 wt % or less, in particular, 80 wt % or more and 99.5 wt % or less, based on the total amount of the light-emitting layer.

The concentration of the guest material based on the host material in the light-emitting layer of the organic light-emitting device according to the embodiment is 0.01 wt % or more and 30 wt % or less, in particular, 0.1 wt % or more and 20 wt % or less.

The light-emitting layer may be a monolayer or a multilayer. For example, a white-light-emitting device may have any of the light-emitting layer configurations shown below, but the configuration is not limited thereto:

(1) Monolayer: a device containing blue-, green-, and red-light-emitting materials;
(2) Monolayer: a device containing pale-blue- and yellow-light-emitting materials;
(3) Two-layer: a layered device composed of a blue-light-emitting layer and a light-emitting layer containing green- and red-light-emitting materials or composed of a red-light-emitting layer and a light-emitting layer containing blue- and green-light-emitting materials;
(4) Two-layer: a layered device composed of a pale-blue-light-emitting layer and a yellow-light-emitting layer; and
(5) Three-layer: a layered device composed of a blue-light-emitting layer, a green-light-emitting layer, and a red-light-emitting layer.

In the case of that the organic light-emitting device according to the embodiment emits white light, the light-emitting layers emit light of different colors, i.e., red, green, and blue, and white light is emitted by mixing the respective luminescent colors. The material emitting red light can be the organic compound according to the embodiment.

The organic white-light-emitting device according to the embodiment may be of a configuration having a plurality of light-emitting layers or a configuration having a light-emitting portion including a plurality of light-emitting materials. In such a case, one of the materials contained in the light-emitting portion is the organic compound according to the present invention.

FIG. 1 is a schematic cross-sectional view illustrating a device configuration having a lamination type light-emitting layer, which is an example of the organic white-light-emitting device according to the embodiment. This drawing shows an organic light-emitting device having three light-emitting layers that emit light of different colors. The structure will be described in detail below.

This organic light-emitting device has a device configuration where an anode 1, a hole-injecting layer 2, a hole-transporting layer 3, a blue-light-emitting layer 4, a green-light-emitting layer 5, a red-light-emitting layer 6, an electron-transporting layer 7, an electron-injecting layer 8, and a cathode 9 are laminated on a substrate such as a glass substrate. The order of the lamination of the blue-, green-, and red-light-emitting layers may be changed.

The configuration of the light-emitting layers is not limited to lamination, and the layers may be horizontally arranged. In the horizontal arrangement, every light-emitting layer is in contact with the adjacent layers such as a hole-transporting layer and an electron-transporting layer.

The light-emitting layer may have a configuration where a single light-emitting layer includes a plurality of light-emitting materials emitting light of different colors. In such a case, the light-emitting materials may form the respective domains.

In the white-light-emitting device according to the embodiment, the light-emitting material of the blue-light-emitting layer, the light-emitting material of the green-light-emitting layer, and the light-emitting material of the red-light-emitting layer are not particularly limited. For example, compounds having a chrysene skeleton, a fluoranthene skeleton, or an anthracene skeleton; boron complexes; or iridium complexes can be used.

The white color according to the embodiment includes pure white and neutral white color. The white color according to the embodiment has a color temperature of 3000 to 9500 K. The emission of the organic white-light-emitting device according to the embodiment has C.I.E. chromaticity coordinates of x in the range of 0.25 to 0.50 and y in the range of 0.30 to 0.42.

In the organic light-emitting device according to the embodiment, in addition to the compound according to the present invention, for example, a known hole-injecting material, hole-transporting material, host material, guest material, electron-injecting material, or electron-transporting material can be optionally used. These materials may be a low-molecular compound or a high-molecular compound.

Examples of these compounds are shown below.

As the hole-injecting or transporting material, a material having high hole mobility can be used. Examples of the low- or high-molecular material having hole-injecting or transporting ability include, but not limited to, triarylamine derivatives, phenylenediamine derivatives, stilbene derivatives, phthalocyanine derivatives, porphyrin derivatives, poly(vinylcarbazole), poly(thiophene), and other electrically conductive polymers.

Examples of the host material include, but not limited to, triarylamine derivatives, phenylene derivatives, fused ring aromatic compounds (e.g., naphthalene derivatives, phenanthrene derivatives, fluorene derivatives, and chrysene derivatives), organic metal complexes (e.g., organic aluminum complexes such as tris(8-quinolinolate)aluminum, organic beryllium complexes, organic iridium complexes, and organic platinum complexes), and polymer derivatives such as poly(phenylenevinylene) derivatives, poly(fluorene) derivatives, poly(phenylene) derivatives, poly(thienylenevinylene) derivatives, and poly(acetylene) derivatives.

Specific structural formulae of the guest compound are shown in Table 3. The guest compound may be derivatives of the compounds having the structural formulae shown in Table 3. Other examples of the guest compound include, but not limited to, fused ring compounds (e.g., fluorene derivatives, naphthalene derivatives, anthracene derivatives, pyrene derivatives, benzofluoranthene derivatives, carbazole derivatives, quinoxaline derivatives, and quinoline derivatives), organic zinc complexes, triphenylamine derivatives, and polymer derivatives such as poly(fluorene) derivatives and poly(phenylene) derivatives.

TABLE 3

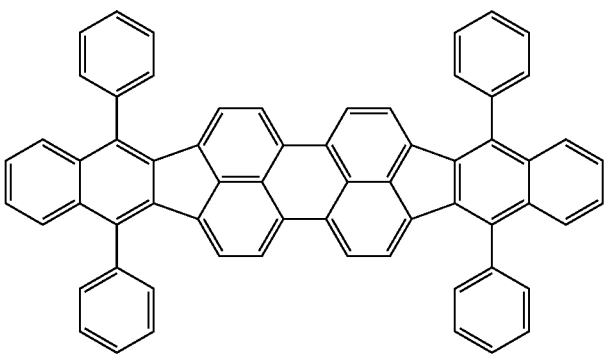 [SMILES: c1ccc(-c2c3c(c(-c4ccccc4)c4ccccc24)-c2ccc4c5ccc6c7c(ccc(c8ccc-3c2c84)c75)-c2c-6c(-c3ccccc3)c3ccccc3c2-c2ccccc2)cc1]

D1

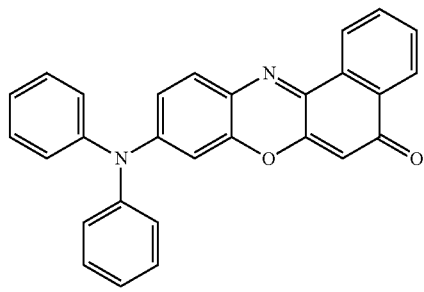 [SMILES: O=c1cc2oc3cc(N(c4ccccc4)c4ccccc4)ccc3nc-2c2ccccc12]

D2

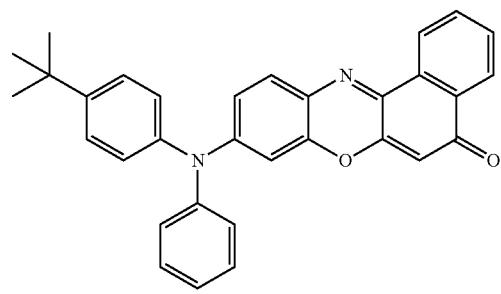 [SMILES: CC(C)(C)c1ccc(N(c2ccccc2)c2ccc3nc4c5ccccc5c(=O)cc-4oc3c2)cc1]

D3

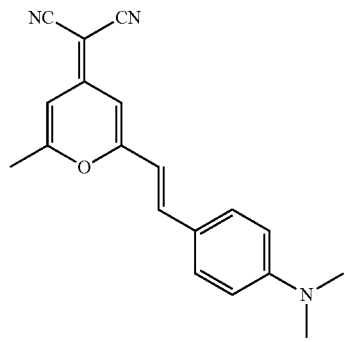

D4

TABLE 3-continued
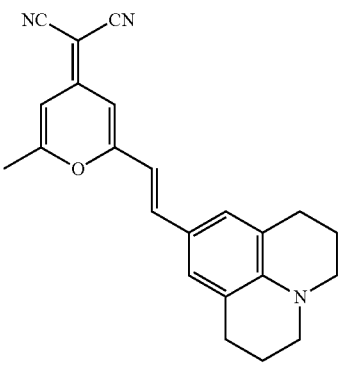 [SMILES: CC1=CC(=C(C#N)C#N)C=C(/C=C/c2cc3c4c(c2)CCCN4CCC3)O1]
D5
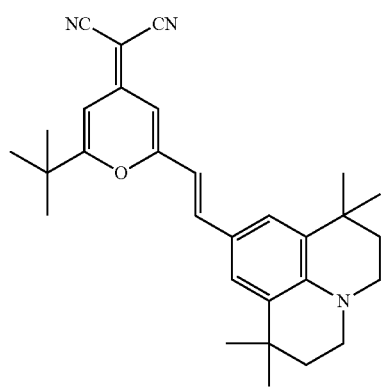 [SMILES: CC(C)(C)C1=CC(=C(C#N)C#N)C=C(/C=C/c2cc3c4c(c2)C(C)(C)CCN4CCC3(C)C)O1]
D6
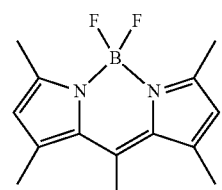
D7
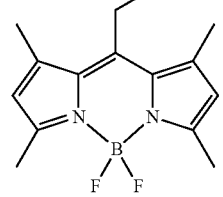
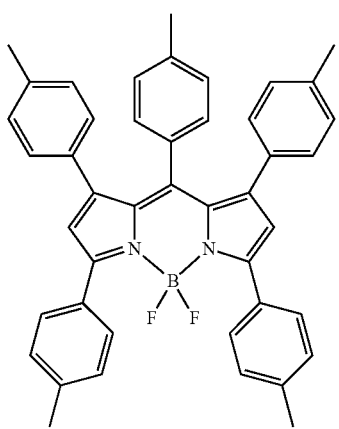
D8

TABLE 3-continued

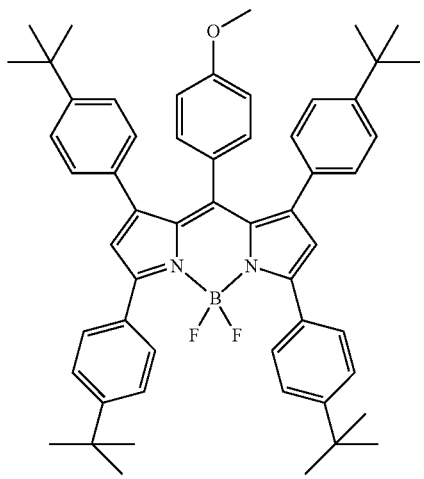

D9

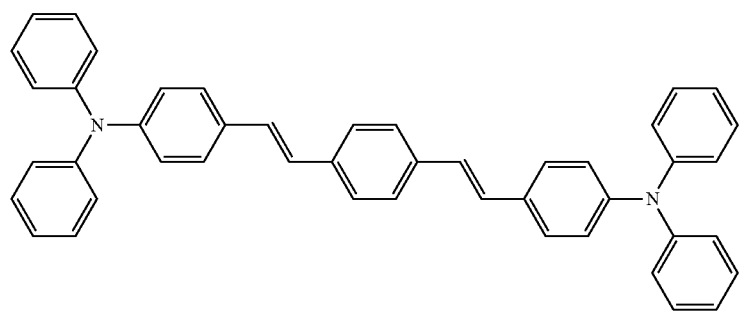 [SMILES: C(=C\c1ccc(N(c2ccccc2)c2ccccc2)cc1)/c1ccc(/C=C/c2ccc(N(c3ccccc3)c3ccccc3)cc2)cc1]

D10

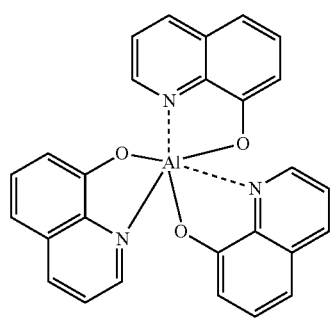

D11

The electron-injecting or transporting material is appropriately selected by considering, for example, the balance with the hole mobility of the hole-injecting or transporting material. Examples of the material having electron-injecting or transporting ability include, but not limited to, oxadiazole derivatives, oxazole derivatives, pyrazine derivatives, triazole derivatives, triazine derivatives, quinoline derivatives, quinoxaline derivatives, phenanthroline derivatives, and organic aluminum complexes.

As the anode material, a material having a higher work function is used. Examples of the material include simple metals such as gold, platinum, silver, copper, nickel, palladium, cobalt, selenium, vanadium, and tungsten; alloys of these simple metals; and metal oxides such as tin oxide, zinc oxide, indium oxide, indium tin oxide (ITO), and indium zinc oxide. In addition, electrically conductive polymers such as polyaniline, polypyrrole, and polythiophene can be used.

These electrode materials may be used alone or in combination. The anode may have a monolayer structure or a multilayer structure.

In contrast, as the cathode material, a material having a lower work function is used. Examples of the material include alkali metals such as lithium; alkaline earth metals such as calcium; simple metals such as aluminum, titanium, manganese, silver, lead, and chromium; and alloys of these simple metals, such as magnesium-silver, aluminum-lithium, and aluminum-magnesium. In addition, metal oxides such as indium tin oxide (ITO) can be used. These electrode materials may be used alone or in combination. The cathode may have a monolayer structure or a multilayer structure.

In the organic light-emitting device according to the embodiment, a layer containing the fused multi-ring compound according to the embodiment and other layers of other organic compounds are formed by the following methods.

For example, a layer is formed by vacuum vapor deposition, ionized vapor deposition, sputtering, plasma coating, or known coating such as spin coating, dipping, a casting method, an LB method, or an ink-jetting method of a compound dissolved in an appropriate solvent.

In the case of forming a layer by vacuum deposition, solution coating, or the like, crystallization hardly occurs, and the resulting layer shows excellent stability for a long time. In addition, in coating, a film can be formed in combination with an appropriate binder resin.

Examples of the binder resin include, but not limited to, polyvinyl carbazole resins, polycarbonate resins, polyester resins, ABS resins, acrylic resins, polyimide resins, phenol resins, epoxy resins, silicone resins, and urea resins.

These binder resins may be used alone as a homopolymer or a copolymer or in combination of two or more thereof. In addition, known additives such as a plasticizer, an antioxidant, or a UV absorber may be optionally used together with the resin binder.

Use of Organic Light-Emitting Device According to the Embodiment

The organic light-emitting device according to the embodiment can be used as a component of a display apparatus or a lighting system. Other examples of use include exposure light sources of electrophotographic image forming apparatuses, backlights of liquid crystal display apparatuses, and white light sources. The organic light-emitting device may further include a color filter. The display apparatus according to the embodiment includes the organic light-emitting device according to the embodiment in a display section. This display section includes a plurality of pixels.

The pixels each include the organic light-emitting device according to the embodiment and an active device. Examples of the active device include switching devices and amplifier devices for controlling luminance. An example of these active devices is a transistor. The anode or the cathode of the organic light-emitting device is connected to the active device. Here, the display apparatus can be used as an image display apparatus of, for example, a PC.

The display apparatus may be an image display apparatus that includes an image input section for inputting image information from, for example, an area CCD, a linear CCD, or a memory card and displays the input image on the display section.

The display section of an image pickup apparatus or ink-jet printer may have a touch panel function. The touch panel function may be driven by any drive system.

The display apparatus may be used in the display section of a multi-functional printer.

The lighting system is an apparatus for lighting, for example, a room. The lighting system may emit light of white, neutral white, or any color from blue to red.

The lighting system according to the embodiment includes the organic light-emitting device according to the embodiment and a converter circuit connected to the device. The lighting system may have a color filter.

The converter circuit according to the embodiment converts AC voltage to DC voltage.

In the embodiment, the white color has a color temperature of about 4200 K, and the neutral white color has a color temperature of about 5000 K.

A display apparatus including the organic light-emitting device according to the embodiment will now be described with reference to FIG. 2.

Figure 2:
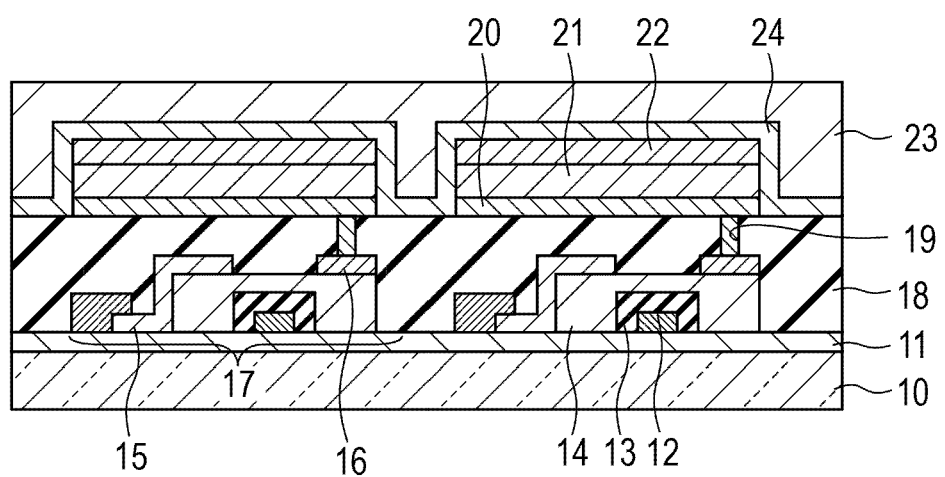
FIG. 2 is a schematic cross-sectional view illustrating an example of the display apparatus having organic light-emitting devices according to the embodiment and switching devices connected to the organic light-emitting devices.

FIG. 2 is a schematic cross-sectional view of a display apparatus having organic light-emitting devices according to the embodiment and TFT devices as an example of transistors connected to the organic light-emitting devices.

The display apparatus includes a substrate 10 such as a glass substrate and a moisture-proof film 11 disposed on the substrate 10 for protecting the TFT devices or the organic compound layer. Reference numeral 12 denotes a metal gate electrode, reference numeral 13 denotes a gate insulating film, and reference numeral 14 denotes a semiconductor layer.

The TFT device 17 includes a semiconductor layer 14, a drain electrode 15, and a source electrode 16. An insulating film 18 is disposed on the TFT device 17. The anode 20 of the organic light-emitting device and the source electrode 16 are connected to each other via a contact hole 19.

The display apparatus according to the embodiment is not limited to this configuration as long as either the anode or the cathode is connected to either the source electrode or the drain electrode of the TFT device.

In FIG. 2, the organic compound layer 21 of a multilayer is shown as one layer. The organic compound layer may be composed of a plurality of layers. Furthermore, a first protective layer 23 and a second protective layer 24 are disposed on the cathode 22 to prevent the organic light-emitting device from deteriorating.

The display apparatus according to the embodiment can emit white light by, for example, using the lamination type light-emitting layer shown in FIG. 1 as the organic compound layer 21 shown in FIG. 2.

The light-emitting layers of the display apparatus that emits white light according to the embodiment are not limited to the device configuration shown in FIG. 1. The light-emitting layers that emit light of different colors may be horizontally arranged, or materials emitting light of different colors may form the respective domains in a single light-emitting layer.

The display apparatus according to the embodiment may use an MIM device instead of the transistor as a switching device.

The transistor is not limited to transistors using single-crystalline silicon wafers and may be a thin film transistor having an active layer on the insulating surface of a substrate. The thin film transistor may be a thin film transistor using single crystal silicon as the active layer, a thin film transistor using non-single crystalline silicon such as amorphous silicon or fine-crystalline silicon as the active layer, or a thin film transistor using non-single crystalline oxide semiconductor such as indium zinc oxide (IZO) or indium gallium zinc oxide (IGZO) as the active layer. The thin film transistor is also called a TFT device.

The transistor having the organic light-emitting device according to the embodiment may be formed in a substrate such as a Si substrate. The term "in a substrate" means that a transistor is formed by processing the substrate, such as a Si substrate, itself. That is, having a transistor in a substrate is that the substrate and the transistor are integrally formed.

The configuration is selected depending on the resolution. For example, in a resolution of about 1-inch QVGA, the organic light-emitting devices can be disposed in a Si substrate.

It is possible to stably display an image with high quality for a long time by driving a display apparatus including the organic light-emitting devices according to the embodiment.

The compounds according to the present invention can also be used in an in vivo label or filter film, in addition to the organic light-emitting device.

EXAMPLES

Example 1

Synthesis of Example Compound A1

[Chem. 14]

A 300-mL two-necked recovery flask was charged with 6.00 g (38.2 mmol) of compound E1, 1.37 g (57.3 mmol) of magnesium, and 30 mL of diethyl ether, followed by stirring under a nitrogen gas flow for 1 hour.

Subsequently, 9.04 g (25.5 mmol) of compound E2, 832 mg (1.02 mmol) Pd(dppf), 50 mL of diethyl ether, and 1.07 g (25.5 mmol) of lithium chloride were added to the 300-mL two-necked recovery flask, followed by stirring under a nitrogen gas flow at 50° C. for 8 hours.

After completion of the reaction, water and toluene were added to the reaction solution. Subsequently, the organic layer was recovered by solvent extraction operation and dried over sodium sulfate.

The solvent was removed from the organic layer by distillation under reduced pressure, and the resulting residue was purified by silica gel column chromatography (mobile phase: chloroform:heptane=1:5) to give 6.28 g (yield: 87%) of compound E3 as a colorless transparent liquid.

[Chem. 15]

A 200-mL recovery flask was charged with 2.60 g (9.18 mmol) of compound E3, 3.53 g (27.5 mmol) of compound E4, 2.79 mg (27.5 mmol) of triethylamine, 498 mg of Ni(dppp)Cl$_2$, and 30 mL of toluene, followed by stirring under a nitrogen gas flow at 95° C. for 5 hours.

After completion of the reaction, water and toluene were added to the reaction solution. Subsequently, the organic layer was recovered by solvent extraction operation and dried over sodium sulfate.

Subsequently, the solvent was removed from the organic layer by distillation under reduced pressure, and the resulting residue was purified by silica gel column chromatography (mobile phase: toluene:heptane=1:1) to give 1.70 g (yield: 56%) of compound E5 as a white solid.

[Chem. 16]

A 200-mL recovery flask was charged with 6.47 g (41.2 mmol) of compound E7 and a THF solution, followed by stirring under a nitrogen gas flow at −78° C. for 1 hour. To this solution, 25.8 mL (41.2 mmol) of a 1.6 M n-BuLi-hexane solution was gradually added at −78° C., followed by stirring under a nitrogen gas flow for 1 hour.

Subsequently, 4.56 g (16.5 mmol) of compound E6 was added to the reaction solution, followed by stirring at room temperature overnight under a nitrogen gas flow. After completion of the reaction, water and dichloromethane were added to this reaction solution. Subsequently, the organic layer was recovered by solvent extraction operation and dried over sodium sulfate.

The solvent was removed from the organic layer by distillation under reduced pressure, and the resulting residue was washed by dispersing in a solvent mixture of chloroform and heptane to give 5.85 g (yield: 82%) of compound E8 as a white solid.

[Chem. 17]

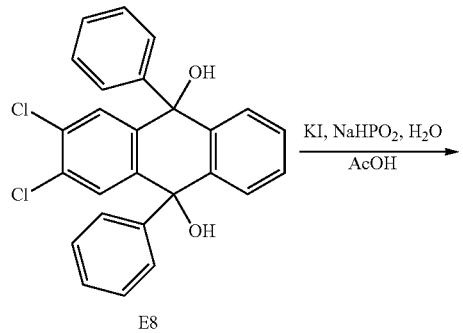

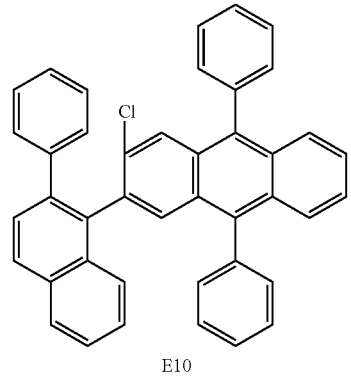

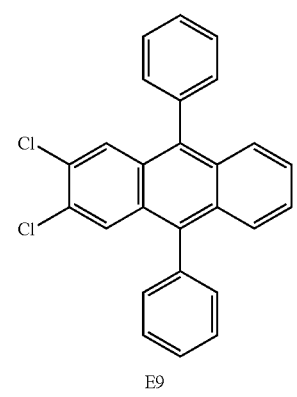

A 200-mL recovery flask was charged with 4.58 g (10.5 mmol) of compound E8, 2.10 g (12.7 mmol) of potassium iodide, 1.34 g (12.7 mmol) of $NaH_2PO_2 \cdot H_2O$, and 90 mL of acetic acid, followed by stirring under a nitrogen gas flow at 100° C. for 1 hour.

Water was added to the reaction solution after completion of the reaction, and the precipitate was recovered. Subsequently, the precipitate was washed by dispersing in methanol to give a crude product. The resulting crude product was purified by silica gel column chromatography (mobile phase: toluene:heptane=1:1) to give 2.88 g (yield: 68%) of compound E9 as a light yellow solid.

[Chem. 18]

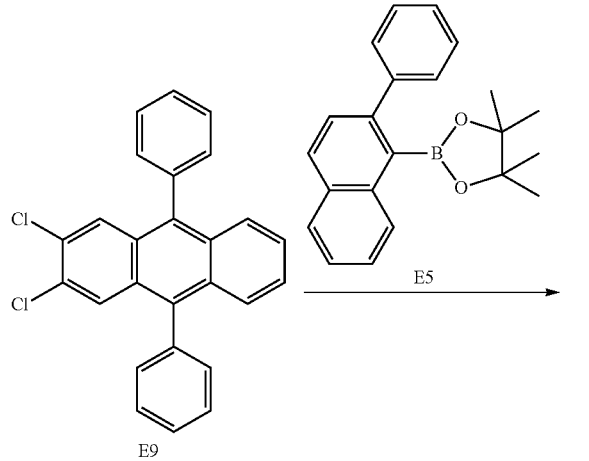

A 200-mL recovery flask was charged with 695 mg (2.11 mmol) of compound E5, 700 mg (1.75 mmol) of compound E9, 291 mg (0.71 mmol) of 2-dicyclohexylphosphino-2',6'-dimethoxybiphenyl, 121 mg (0.21 mmol) of $Pd(dba)_2$, 928 mg (4.38 mmol) of $K_3PO_4$, and 30 mL of toluene, followed by stirring under a nitrogen gas flow at 100° C. for 3 hours.

After completion of the reaction, water and toluene were added to the reaction solution. Subsequently, the organic layer was recovered by solvent extraction operation and dried over sodium sulfate.

The solvent was removed from the organic layer by distillation under reduced pressure, and the resulting residue was purified by silica gel column chromatography (mobile phase: chloroform:heptane=1:3) to give 810 mg (yield: 82%) of compound E10 as a light yellow solid.

[Chem. 19]

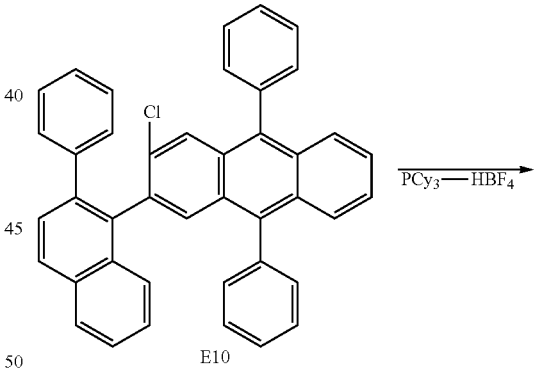

A 50-mL of recovery flask was charged with 820 mg (1.44 mmol) of compound E10, 40 mg (0.17 mmol) of palladium acetate, 128 mg (0.35 mmol) of PCy$_3$-HBF$_4$, 497 mg (3.60 mmol) of potassium carbonate, and 10 mL of N,N-dimethylacetamide, followed by stirring under a nitrogen gas flow at 140° C. for 4 hours.

After completion of the reaction, water and toluene were added to the reaction solution. Subsequently, the organic layer was recovered by solvent extraction operation and dried over sodium sulfate.

The solvent was removed from the organic layer by distillation under reduced pressure, and the resulting residue was purified by silica gel column chromatography (mobile phase: chloroform:heptane=1:3) to give 427 mg (yield: 56%) of Example Compound A1 as a yellow solid.

Four hundred milligrams of the resulting Example Compound A1 was subjected to sublimation purification at a degree of vacuum of $7.0\times10^{-1}$ Pa, an argon gas flow of 10 mL/min, and a sublimation temperature of 320° C. with a sublimation purification apparatus manufactured by Ulvac Kiko Inc. to give 370 mg of highly purified Example Compound A1.

The resulting compound was identified by mass spectrometry.

Matrix-assisted laser desorption ionization time-of-flight mass spectrometry (MALDI-TOF-MS):

Observed value: m/z=530.52, calculated value: C$_{42}$H$_{26}$O=530.66.

The energy gap of Example Compound A1 was measured by the following process.

Example Compound A1 was vapor-deposited on a glass substrate to form a vapor-deposited thin film having a thickness of 20 nm. The absorption spectrum of this vapor-deposited thin film was measured with an ultraviolet and visible spectrophotometer (V-560, manufactured by JASCO Corp.). The energy gap of Example Compound A1 was determined to be 2.5 eV from the absorption edge of the resulting absorption spectrum.

Example 2

Synthesis of Example Compound A4

Example Compound A4 was prepared by the same reaction and purification processes as those in Example 1 except that organic compound E11 was used in place of organic compound E7 in Example 1.

[Chem. 20]

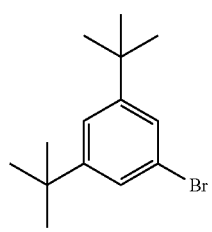

E11

The resulting compound was identified by mass spectrometry.

MALDI-TOF-MS:

Observed value: m/z=755.58, calculated value: C$_{58}$H$_{58}$=755.08.

The energy gap of Example Compound A4 was measured as in Example 1.

The energy gap of Example Compound A4 was 2.3 eV.

Example 3

Synthesis of Example Compound A6

Example Compound A6 was prepared by the same reaction and purification processes as those in Example 1 except that organic compound E12 was used in place of organic compound E7 in Example 1.

[Chem. 21]

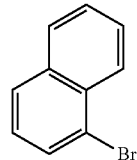

E12

The resulting compound was identified by mass spectrometry.

MALDI-TOF-MS:

Observed value: m/z=630.22, calculated value: C$_{50}$H$_{30}$=630.77.

The energy gap of Example Compound A6 was measured as in Example 1.

The energy gap of Example Compound A6 was 2.6 eV.

Example 4

Synthesis of Example Compound A10

Example Compound A10 was prepared by the same reaction and purification processes as those in Example 1 except that organic compound E13 was used in place of organic compound E1 in Example 1.

[Chem. 22]

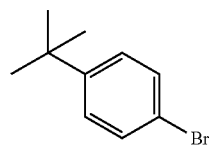

E13

The resulting compound was identified by mass spectrometry.

MALDI-TOF-MS:

Observed value: m/z=586.20, calculated value: C$_{46}$H$_{34}$=586.76.

The energy gap of Example Compound A10 was measured as in Example 1.

The energy gap of Example Compound A10 was 2.5 eV.

Example 5

Synthesis of Example Compound A14

Example Compound A14 was prepared by the same reaction and purification processes as those in Example 1 except that organic compound E14 was used in place of organic compound E2 in Example 1.

[Chem. 23]

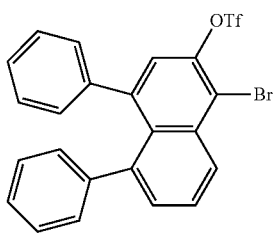

E14

The resulting compound was identified by mass spectrometry.

MALDI-TOF-MS:

Observed value: m/z=682.52, calculated value: $C_{54}H_{34}$=682.85.

The energy gap of Example Compound A14 was measured as in Example 1.

The energy gap of Example Compound A14 was 2.5 eV.

Comparative Example 1

Synthesis of Comparative Compound (2)

Comparative Compound (2) was prepared by the same reaction and purification processes as those in Example 1 except that organic compound E15 was used in place of organic compound E9 in Example 1.

[Chem. 24]

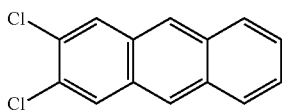

E15

Example 6

In this example, a multilayered-type organic light-emitting device (anode/hole-injecting layer/hole-transporting layer/light-emitting layer/electron-transporting layer/electron-injecting layer/cathode) was produced. An ITO film was formed on a glass substrate by patterning so as to have a thickness of 100 nm to form an ITO substrate.

On the resulting ITO substrate, the following organic compound layers and electrodes were sequentially formed by resistance heating vacuum vapor deposition in a vacuum chamber of $10^{-5}$ Pa such that the facing area of the electrodes is 3 mm². The structure of compound D1 is shown in Table 3.

Hole-injecting layer (30 nm): compound F1

Hole-transporting layer (10 nm): compound F2

Light-emitting layer (30 nm): host: compound A1 (weight ratio: 99.5%), guest: compound D1 (weight ratio: 0.5%)

Electron-transporting layer (30 nm): compound F4

Electron-injecting layer (1 nm): LiF

Metal electrode layer (100 nm): Al

[Chem. 25]

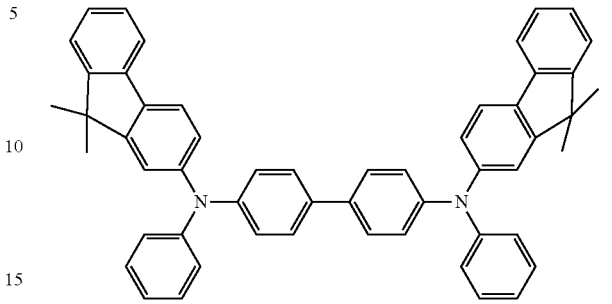

F1

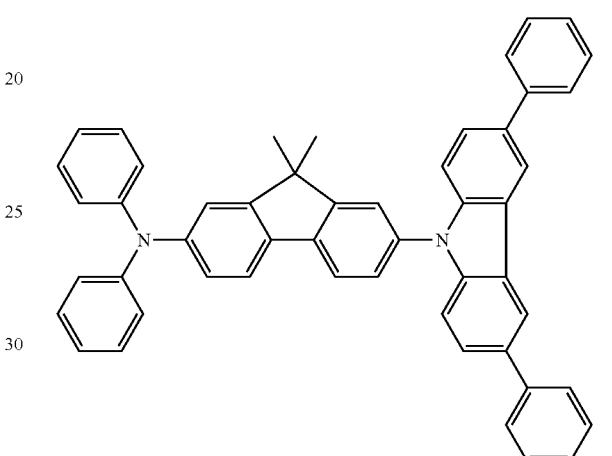

F2

F3

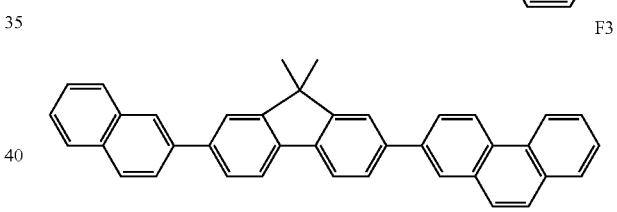

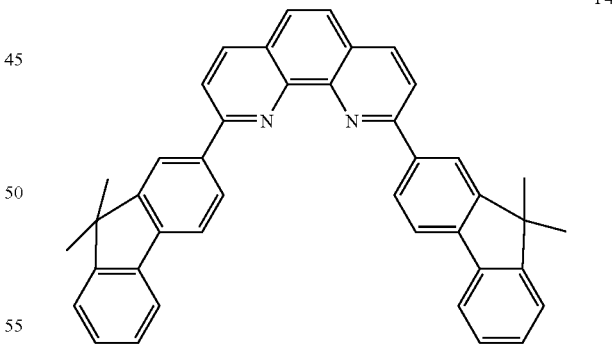

F4

A voltage of 5.2 V was applied to the resulting organic light-emitting device using the ITO electrode as the positive electrode and the Al electrode as the negative electrode to observe red light emission with a luminous efficiency of 4.8 cd/A and a luminance of 2000 cd/m².

In order to evaluate the stability of the resulting device, the time till the luminance decreases by 10% in driving at an initial luminance of 4500 cd/m² was measured and was confirmed to exceed 70000 hours.

Examples 7 to 11 and Comparative Example 2

Devices were produced as in Example 6 except that the host materials and the guest materials in light-emitting layers were changed to those shown in Table 4. The resulting devices were evaluated as in Example 6. The results are shown in Table 4.

TABLE 4

| | Host | Guest | Luminous efficiency (cd/A) | Voltage (V) | Luminescent color | Lifetime for 10% reduction (hr) |
|---|---|---|---|---|---|---|
| Example 7 | A4 | D1 | 4.7 | 5.4 | Red | 72000 |
| Example 8 | A6 | D2 | 5.2 | 5.4 | Red | 65000 |
| Example 9 | A10 | D1 | 4.9 | 5.2 | Red | 70000 |
| Example 10 | A17 | D1 | 5.3 | 5.1 | Red | 60000 |
| Example 11 | A1 | D10 | 4.1 | 4.9 | Green | 10000 |
| Comparative Example 2 | Compound (2) | D1 | 2.3 | 5.2 | Red | 30000 |

Example 12

In this example, an organic light-emitting device having a resonance structure was produced by the following process.

An aluminum alloy (AlNd) film serving as a reflective anode was formed on a support of a glass substrate by sputtering so as to have a thickness of 100 nm.

Then, an ITO film serving as a transparent anode was formed thereon by sputtering so as to have a thickness of 80 nm. Furthermore, a device isolation film of polyimide having a thickness of 1.5 μm was formed at the peripheral region of the anode, and an opening having a radius of 3 mm was formed therein.

The resulting product was washed by ultrasonic cleaning with acetone and then isopropyl alcohol (IPA) and then washed by boiling in IPA, followed by drying. Furthermore, the surface of this substrate was washed with UV.

Furthermore, organic layers shown below were sequentially formed by resistance heating vacuum vapor deposition in a vacuum chamber of $10^{-5}$ Pa, and then a transparent electrode having a thickness of 30 nm was formed as a cathode by sputtering IZO. After the formation, sealing was performed in a nitrogen atmosphere. Thus, an organic light-emitting device was formed.

Hole-injecting layer (185 nm): compound F1
Hole-transporting layer (10 nm): compound F2
Light-emitting layer (35 nm): host: compound A1 (weight ratio: 99.5%), guest: compound D1 (weight ratio: 0.5%)
Electron-transporting layer (10 nm): compound F3
Electron-injecting layer (70 nm): compound F4 (weight ratio: 80%), Li (weight ratio: 20%)

A voltage of 4.6 V was applied to the resulting organic light-emitting device using the ITO electrode as the positive electrode and the IZO electrode as the negative electrode to observe red light emission with a luminous efficiency of 10.6 cd/A and a luminance of 2000 cd/m².

Example 13

In this example, an organic white-light-emitting device having a configuration composed of anode/hole-injecting layer/hole-transporting layer/red-light-emitting layer/green-light-emitting layer/blue-light-emitting layer/electron-transporting layer/electron-injecting layer/cathode disposed in this order on a substrate was produced by the following process.

A film of ITO serving as an anode was formed on a glass substrate by sputtering so as to have a thickness of 120 nm, and the resulting product was used as a transparent electrically conductive support substrate (ITO substrate).

On this ITO substrate, organic compound layers and electrode layers shown below were sequentially formed by resistance heating vacuum vapor deposition in a vacuum chamber of $10^{-5}$ Pa. On this occasion, the area of electrodes facing each other was adjusted to be 3 mm².

Hole-injecting layer (30 nm): compound F1
Hole-transporting layer (10 nm): compound F2
Red-light-emitting layer (15 nm): host 1: compound A1 (weight ratio: 98.5%), host 2: compound F6 (weight ratio: 1.0%), guest: compound D1 (weight ratio: 0.5%)
Green-light-emitting layer (5 nm): host: compound F4 (weight ratio: 95.0%), guest: compound D10 (weight ratio: 5.0%)
Blue-light-emitting layer (20 nm): host: compound F4 (weight ratio: 95.0%), guest: compound F5 (weight ratio: 5.0%)
Electron-transporting layer (30 nm): compound F3
Electron-injecting layer (1 nm): LiF
Metal electrode layer (100 nm): Al

[Chem. 26]

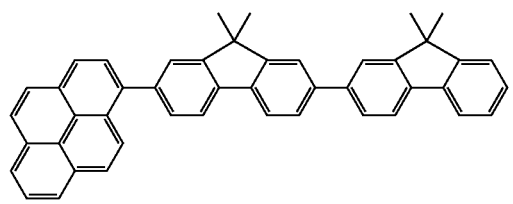

F4

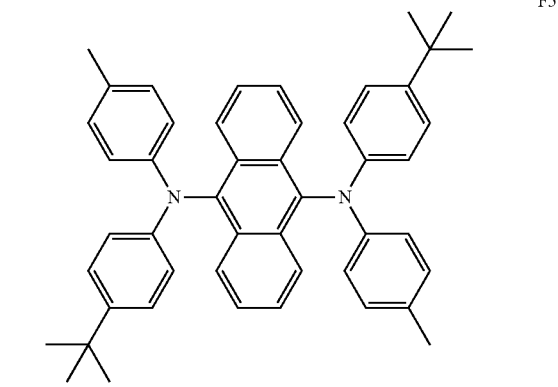

F5

A voltage was applied to the resulting organic light-emitting device using the ITO electrode as the positive electrode and the Al electrode as the negative electrode to observe white light emission with C.I.E. chromaticity coordinates of (0.32, 0.35).

RESULTS AND CONCLUSION

As described above, an organic red-light-emitting device with a long lifetime can be provided by using a novel fused ring compound according to the present invention as a host material in the light-emitting layer. In addition, a white-light-emitting device can be provided by using the fused ring compound together with materials that emit light of other colors.

Effect of Present Invention

According to the present invention, an organic compound being stable against oxidation and having a high amorphous property can be provided. Furthermore, an organic light-emitting device showing high luminous efficiency and a long device lifetime can be provided by using the organic compound in the device.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-256747, filed Nov. 24, 2011, which is hereby incorporated by reference herein in its entirety.

REFERENCE SIGNS LIST 4 blue-light-emitting layer
5 green-light-emitting layer
6 red-light-emitting layer
17 TFT device
20 anode
21 organic compound layer
22 cathode

The invention claimed is:
1. An organic compound represented by the following Formula [1]:

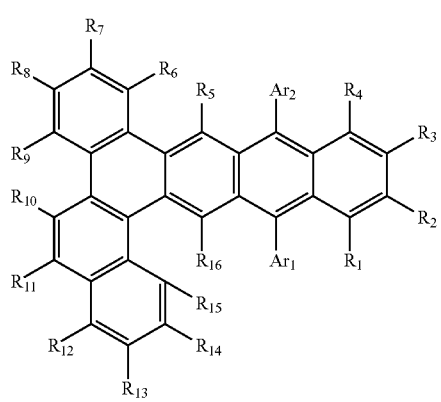

[1]

wherein,
$R_1$ to $R_{16}$ are each independently selected from the group consisting of a hydrogen atom, a halogen atom, an alkyl group having 1 to 4 carbon atoms, a cyano group, a diphenylamino group, a pyridyl group, and an aryl group, wherein
the diphenylamino group, the pyridyl group, and the aryl group each optionally have at least one substituent selected from the group consisting of a methyl group, an ethyl group, an iso-propyl group, a t-butyl group, and a fluorine atom; and
$Ar_1$ and $Ar_2$ are each any of a phenyl group, a biphenyl group, a terphenyl group, and a naphthyl group, wherein
$Ar_1$ and $Ar_2$ each optionally have at least one substituent selected from the group consisting of a methyl group, an ethyl group, an iso-propyl group, a t-butyl group, and a fluorine atom.

2. The organic compound according to claim 1, represented by the following Formula [2]:

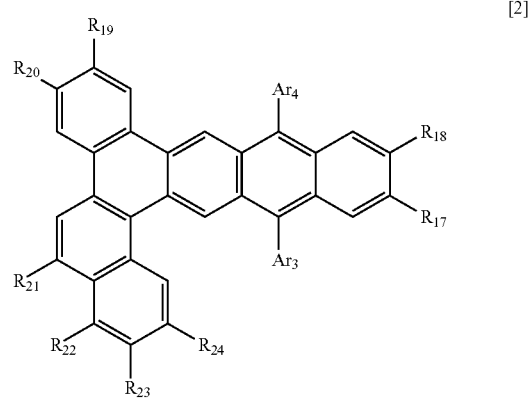

[2]

wherein,
$R_{17}$ to $R_{24}$ are each independently selected from the group consisting of a hydrogen atom, a halogen atom, an alkyl group having 1 to 4 carbon atoms, a cyano group, a diphenylamino group, a pyridyl group, and an aryl group, wherein
the diphenylamino group, the pyridyl group, and the aryl group each optionally have at least one substituent selected from the group consisting of a methyl group, an ethyl group, an iso-propyl group, a t-butyl group, and a fluorine atom; and
$Ar_3$ and $Ar_4$ are each any of a phenyl group, a biphenyl group, a terphenyl group, and a naphthyl group, wherein
$Ar_3$ and $Ar_4$ each optionally have at least one substituent selected from the group consisting of a methyl group, an ethyl group, an iso-propyl group, a t-butyl group, and a fluorine atom.

3. An organic light-emitting device comprising a pair of electrodes and an organic compound layer disposed between the pair of electrode, wherein
the organic compound layer includes an organic compound according to claim 1.

4. The organic light-emitting device according to claim 3, wherein the organic compound layer is a light-emitting layer.

5. The organic light-emitting device according to claim 4, wherein the light-emitting layer includes a host material and a guest material, and the host material is the organic compound represented by Formula [1].

6. The organic light-emitting device according to claim 3, wherein
- the organic compound layer includes a light-emitting portion including a plurality of organic compounds;
- at least one of the plurality of organic compounds is the organic compound represented by Formula [1]; and
- the light-emitting portion emits white light.

7. A display apparatus comprising:
- a plurality of pixels each including an organic light-emitting device according to claim 3 and a transistor connected to the organic light-emitting device.

8. The display apparatus according to claim 7, wherein
- the organic light-emitting device is disposed on a substrate; and
- the substrate has the transistor therein.

9. An image display apparatus comprising:
- an input section for inputting image information and a display section for displaying an image, wherein
- the display section includes a plurality of pixels each including an organic light-emitting device according to claim 3 and a transistor connected to the organic light-emitting device.

10. A lighting system comprising:
- an organic light-emitting device according to claim 3; and
- a converter circuit connected to the organic light-emitting device.

* * * * *